United States Patent [19]  
Senter

[11] Patent Number: 4,952,394  
[45] Date of Patent: Aug. 28, 1990

[54] DRUG-MONOCLONAL ANTIBODY CONJUGATES

[75] Inventor: Peter D. Senter, Seattle, Wash.

[73] Assignee: Bristol-Myers Company, New York, N.Y.

[21] Appl. No.: 124,313

[22] Filed: Nov. 23, 1987

[51] Int. Cl.$^5$ .................... A61K 39/44; C07K 15/28; C07K 17/00
[52] U.S. Cl. .................... 424/85.91; 530/390; 530/391; 530/389
[58] Field of Search .................... 424/85.91; 530/390, 530/402, 404, 389; 560/32; 514/885

[56] References Cited  
U.S. PATENT DOCUMENTS 4,487,714 12/1984 Kato et al. .................... 530/391  
4,671,958 6/1987 Rodwell et al. .................... 424/85.91

OTHER PUBLICATIONS

Helstrom et al., (1986) Proc. Natl. Acad. Sci. 83: 7059–7063.
Ohkawa et al., (1986) Cancer Immunol. Immunother. 23:81–86.
Rowland et al., (1986) Cancer Immunol. Immunother 21:183–187.
Moller, G. (Ed), *Immunol. Rev.* 62 (1982).
Worrell, et al., Effect of Linkage Variation on Pharmacokinetics of Ricin A Chain–Antibody Conjugates in Normal Rats, *Anti–Cancer Drug Design*, pp. 179–188, (1986).
Saretorelli, Allan C., The Role of Mitomycin Antibiotics in the Chemotherapy of Solid Tumors, *Biochemical Pharmacology*, 35, No. 1, pp. 67–69, (1986).
Gallego, et al., Preparation of Four Daumonycin–Monoclonal Antibody 791T/36 Conjugates with Antitumor Activity, *Int. J. Cancer*, 33, 737–744 (1984).
Endo, et al., In Vitro Cytoxicity of a Human Serum–Albumin–Mediated Conjugate of a Methotrexate With Anti-MM46 Monoclonal Antibody, *Cancer Research*, 47, 1076–1080 (1987).
Teicher and Sartorelli, Design of Models For Testing Cancer Therapeutic Agents, Van Nostrand Reinhold Co., N.Y., pp. 19–36 (1982).

*Primary Examiner*—Garnette Draper  
*Assistant Examiner*—Kay K. Kim  
*Attorney, Agent, or Firm*—Michelle A. Cepeda

[57] ABSTRACT

There is disclosed a drug-monoclonal antibody conjugate wherein the antibody is linked to a antitumor drug using disulfide benzyl carbamate or carbonate as the linker. Also disclosed is a method of delivering an active antitumor drug to the site of tumor cells in a mammal by administering the drug-monoclonal antibody conjugate.

6 Claims, 3 Drawing Sheets 1. para isomer
2. ortho isomer 4. (MMC)

DRUG-MONOCLONAL ANTIBODY CONJUGATES

CROSS-REFERENCE

This application Ser. No. 07/124,314 is related to the application entitled "Anti-Tumor Prodrugs" of Peter D. Senter owned by the assignee of this application and filed concurrently with this application.

BACKGROUND OF THE INVENTION

This invention relates to methods for the delivery of cytotoxic agents to tumor cells.

The use of tumor-associated monoclonal antibodies as carriers for cytotoxic agents has received considerable attention in the past several years (Moller, 1982). The objective of much of this work has been to improve the efficacy of anticancer drugs while diminishing the undesired and often times toxic side-effects. Investigations have been undertaken or proposed to accomplish this objective by use of antibody-drug conjugates in which the antibody serves to deliver the anticancer drug to the tumor.

In order for this approach to be effective, it is necessary that the antibody be highly tumor selective and that the drug be delivered in an active, cytotoxic form. Drugs such as methotrexate (Endo, 1987), daunomycin (Gallego et al., 1984), mitomycin C (MMC) (Ohkawa et al., 1986) and vinca alkaloids (Rowland et al., 1986) have been attached to antibodies and the derived conjugates have been investigated for anti-tumor activities. In many cases, the sporatic activities of such conjugates can be attributed to the diminished activity of the drug when covalently attached to the antibody. Many examples exist in the art which illustrate linkage of antibodies to drugs by means of relatively stable chemical bonds which undergo slow non-specific release e.g. hydrolysis.

Additional problems may arise when the drug is released from the antibody, however, in a chemically modified form. Although the drug may now have access to its site of activity, the chemically modified drug can be significantly less potent.

Because of these considerations, there is a need for the development of new linking strategies, i.e. new drug-antibody conjugates, that can release chemically unmodified drug from the antibody in such a way that the drug can exert its maximal level of activity. Studies have shown that prodrug compounds that are benzyl carbamate disulfide derivatives of mitomycin C(MMC), mitomycin A (MMA), and daunomycin release chemically unmodified drug when the disulfide bond is reduced (Senter, cross-referenced patent application; see FIG. 1).

I have conceived that a prodrug strategy that relies on disulfide bond reduction for drug release may be ideally suited for the delivery of drugs to tumors with tumor associated antibodies since many solid tumors have been shown to exist in oxygen-deficient environments and possess enhanced levels of reducing agents such as glutathione, NADH and NADPH (Sartorelli, 1986). These reducing agents can effect the release of free drug from benzyl carbamate disulfide drug conjugates by reduction of the disulfide bond.

The use of benzyl carbamate disulfide linkers for drugantibody conjugates may also be of use for the intracellular release of drugs in cases where the antibody is taken up inside the cell by receptor-mediated endocytosis. Intracellular thiols such as glutathione could then reduce the disulfide-linked conjugates.

SUMMARY OF THE INVENTION

This invention is a drug-antibody conjugate wherein the antibody and the drug are linked using disulfide benzyl carbamate, e.g. a MMC-antibody conjugate, or disulfide benzyl carbonate, e.g. an etoposide-antibody conjugate.

In another aspect, this invention is a method for delivering to the site of tumor cells in a mammal an active antitumor drug by administering to the mammal the drug-monoclonal antibody conjugate according to this invention.

It has been demonstrated in the cross-referenced application that disulfide-bond reduction initiates a drug fragmentation process whereby the parent, i.e. unmodified, drug is released in an active, cytotoxic form. Furthermore, the rate of drug release can be controlled by sterically hindering the disulfide. Using the chemistry described in the cross-referenced application, there was no significant loss in drug activity. Substantially the same methodology has been found to be useful for the attachment of amine group-containing drugs, and equivalent hydroxyl group-containing drugs and protein toxins, to antibodies for site-directed immunotherapy.

DETAILED DESCRIPTION OF THE INVENTION

Figure 1:
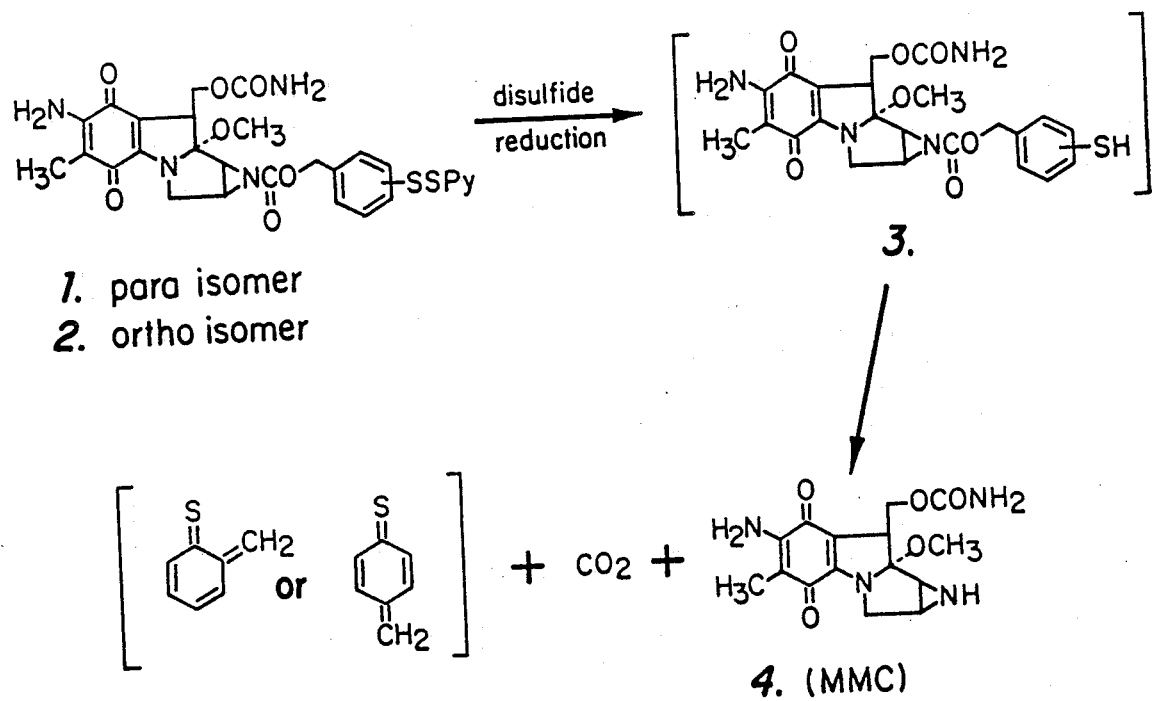
FIG. 1 illustrates the pathway for elimination of MMC from its corresponding prodrug.

This invention is an antitumor drug-monoclonal antibody conjugate having the general structural formula

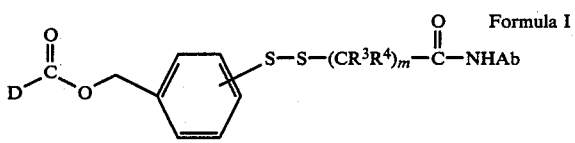

Formula I wherein:

D is an antitumor drug moiety having pendant to the backbone thereof a chemically reactive functional group, by means of which the drug backbone is bonded to the disulfide benzyloxycarbonyl group, derived from the group consisting of a primary amino group represented by the formula $R^1NH-$, a secondary amino group represented by the formula $R^1R^2N-$, and an alcohol group represented by the formula $R^1O-$;

Rwhen $R^1$ and $R^2$ are independent is the backbone of said drug moiety when D is derived from the group consisting of a primary amino group, a secondary amino group, and an alcohol group wherein, in the case of a secondary amino group;

$R^2$, when $R^1$ and $R^2$ are independent, is selected from unsubstituted and substituted, and branched and straight-chain alkyl groups having 1–10 carbon atoms wherein the substituent is selected from 1 to 3 alkoxy groups having 1 to 3 carbon atoms and 1 to 3 halo groups; unsubsituted and substituted phenyl wherein the substituent is selected from 1 to 3 alkyl groups having 1 to 3 carbon atoms, 1 to 3 alkoxy groups having 1 to 3 carbon atoms, and 1 to 3 halo groups; and unsubstituted and substituted phenylalkyl wherein the phenyl moiety, when substituted, is substituted as defined above in the case of substituted phenyl and the alkyl moiety is a polyalkylene group having 1 to 3 carbon atoms;

$R^1$ and $R^2$, when taken together in a functional group derived from a secondary amine, represent the backbone of the drug moiety, D, having a divalent group chemically bonded to the nitrogen atom constituting said secondary amino group;

$R^3$ and $R^4$, independently, are selected from H and unsubstituted and substituted, and branched and straightchain alkyl groups having 1–10 carbon atoms wherein the substituent is selected from 1 to 3 alkoxy groups having 1 to 3 carbon atoms and 1 to 3 halo groups; unsubsituted and substituted phenyl wherein the substituent is selected from 1 to 3 alkyl groups having 1 to 3 carbon atoms, 1 to 3 alkoxy groups having 1 to 3 carbon atoms, and 1 to 3 halo groups; and unsubstituted and substituted phenylalkyl wherein the phenyl moiety, when substituted, is substituted as defined above in the case of substituted phenyl and the alkyl moiety is a polyalkylene group having 1 to 3 carbon atoms;

m is an integer selected from 1 to 10; and

Ab represents a monoclonal antibody having a pendent amino group; and the substitution position of the group, —S—S—$(CR^3R^4)_m$—

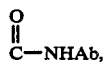

on the phenyl ring of the benzylcarbamate moiety is selected from the ortho- and para-positions.

Representative of said amino group-containing drugs are mitomycin-C, mitomycin-A, daunomycin, adriamycin, aminopterin, actinomycin, bleomycin, and derivatives thereof; and, representative of said alcohol group-containing drugs is etoposide.

The abbreviations used are as follows: MMC, mitomycin C; MMA, mitomycin A; DAU, daunomycin; PBS, phosphate buffered saline; HPLC, high pressure liquid chromatography; DDT, dithiothreitol; and Ab, monoclonal antibody.

In another aspect this invention is a method for delivering to the site of tumor cells in a mammal having enhanced levels of endogenous reducing agents including at least one member of the group of NADH, NADPH and glutathione, an active antitumor drug having pendant to the backbone thereof a chemically reactive functional group selected from the group consisting of a primary amino group represented by the formula, $R^1NH$—, a secondary amino group represented by the formula $R^1R^2N$—, and a alcohol group represented by the formula $R^1O$ wherein $R^1$ and $R^2$ are as defined above, comprising the steps of:

(a) administering to the mammal an antitumor-effective amount of an antitumor drug-monoclonal antibody conjugate having formula I, (b) contacting the antitumor drug-monoclonal antibody conjugate with endogenous reducing conditions, and (c) permitting the antitumor drug-monoclonal antibody conjugate to undergo reductive cleavage to release free drug from the conjugate.

The conjugate according to this invention may be provided for use according to the method of this invention to treat a host, particularly a mammalian host such as, for example, an experimental animal host, affected by a tumor, as a pharmaceutical composition. The pharmaceutical composition comprises a antitumor effective amount, i.e. a tumor growth-inhibiting amount, of the conjugate according to this invention and a pharmaceutically acceptable carrier and optionally, conventional pharmaceutically acceptable excipients and adjuvants.

The antibody component of the immunoconjugate of the invention includes any antibody which binds specifically to a tumor-associated antigen. Examples of such antibodies include, but are not limited to, those which bind specifically to antigens found on carcinomas, melanomas, lymphomas and bone and soft tissue sarcomas as well as other tumors. Antibodies that remain bound to the cell surface for extended periods or that are internalized are preferred. These antibodies may be polyclonal or preferably, monoclonal and can be produced using techniques well established in the art [see, e.g., R. A. DeWeger et al., "Eradication Of Murine Lymphoma And Melanoma Cells By Chlorambucil-Antibody Complexes, *Immunological Rev.*, 62, pp. 29–45 (1982) (tumor-specific polyclonal antibodies produced and used in conjugates) and M. Yeh et al., "Cell Surface Antigens Of Human Melanoma Identified By Monoclonal Antibodies," Proc. Natl. Acad. Sci., 76, p. 2927 (1979) and J. P. Brown et al. "Structural Characterization Of Human Melanoma-Associated Antigen p97 With Monoclonal Antibodies," *J. Immunol.*, 127 (no.2), pp. 539–546 (1981) (tumor-specific monoclonal antibodies produced)].

The pharmaceutical carrier ordinarily will be liquid to provide liquid compositions although liquid compositions would be expected to be more preferred because solid compositions would be expected to have lower absorption from the GI tract. The conjugates according to the invention may be provided as sterile soluble conjugates or compositions which can be dissolved or suspended in sterile water or other liquid medium to provide solutions and suspensions and emulsions for oral administration or for parenteral administration. Examples of liquid carriers suitable for oral administration include water, alcohol, polypropylene glycol, polyethylene glycol and mixtures of two or more of the above. Examples of liquid carriers suitable for parenteral use include water-for-injection, physiological saline, and other suitable sterile injection media. Suitable buffers for use with the liquid carrier to provide, generally, a suitable buffered isotonic solution include trisodium orthophosphate, sodium bicarbonate, sodium citrate, N-methylglucamine, L(+)-lysine, and L(+)-arginine to name but a few representative buffering agents.

The pharmaceutical composition will contain an amount of at least one conjugate of Formula I or mixture of one or more of said compounds of mixture thereof with another antitumor agent. The antitumor effective amount of compound of Formula I may be varied or adjusted widely depending upon the particular application, the form, the potency of the particular conjugate used, and the desired concentration of conjugate in the composition. Generally, the amount of active component will range between about 0.5–90% by weight based on total weight of composition.

In therapeutic use for treating a mammalian host, for example an experimental animal host, affected by a tumor, malignant or benign, the conjugates of this invention will be administered in an amount effective to inhibit the growth of the tumor, that is, a tumor growth-inhibiting amount will be in the range of about 0.1 to about 15 mg/kg of animal body weight/day. It is to be understood that the actual preferred dosage of conjugate will vary widely depending upon the requirements of the animal being treated, the composition being used, and the route of administration. Many factors that modify the action of the anti-neoplastic agent will be taken into account by one skilled in the art to which this invention pertains including, for example, age, body weight and sex of the animal host; diet; time of administration; rate of excretion; condition of the host; severity of the disease; and the like. Administration may be carried out simultaneously or periodically within the maximum tolerated dose. Optimal administration (or application) rates for a given set of conditions may be readily ascertained by those skilled in the art using conventional dosage determination tests.

The following examples are illustrative of the scope and utility of this invention and are not to be construed as limiting the scope of the invention. Unless otherwise indicated, all parts and percentages are by weight and temperatures are in degrees Celsius. The compounds and conjugates are numbered with reference to FIGS. 1 and 2.

EXPERIMENTAL SECTION

Protein A purified monoclonal antibody designated L6 (IgG2a), which reacts to a glycolipid antigen on human lung carcinoma (Hellstrom et al., 1986) was provided by Drs. K. E. and I. Hellstrom (Oncogen, Seattle). The human tumor cell line, A549 was provided by Dr. J. Catino (Bristol-Myers Co., Wallingford).

Conjugate Binding Assay

Immunoconjugates were serially diluted into growth media and 100 µl aliquots were incubated at 4° C. with $1\times10^6$ cells in 100 µl growth media. After one hour, cells were washed twice and resuspended in 100 µl medium containing 1:40 diluted goat anti-mouse IgG-FITC (Boehringer-Mannheim) for 20 minutes at 4° C. Cells were washed and analyzed using a Coulter Epics V fluorescence cell analyzer. For each experiment, similarly diluted MAb was used as a non-conjugated positive binding control.

In Vitro Cytotoxicity Assay.

A549 cells in 0.4 ml of McCoys complete medium were plated at 1000 cells/well in 12-well tissue culture plates and then allowed to incubate overnight at 37° C. The cells were washed with RPMI media and conjugate in 0.4 ml of McCoys media were added. At periodic intervals (1, 3, 6 and 24 hr.), the cells were washed with RPMI to remove any unbound conjugate or drug, fresh McCoys media was added, and incubation was continued at 37° C. for a total of 24 hr. The colonies were stained with crystal violet and were counted with a Optimax 40.10 Image Analyzer.

General Procedure-Preparation of 1 and 2.

A solution of 137 mg (0.55 mmol) of para- or ortho-mercaptobenzyl alcohol, respectively, and 0.044 ml of pyridine (0.55 mmol) in 1 ml of dry dioxane was added over a 3 min period to a stirred solution of 0.032 ml (0.275 mmol) of trichloromethylchloroformate in 0.5 ml of dioxane. After stirring for 15 min., a solution of MMC (92 mg, 0.275 mmol) and triethylamine (0.153 ml, 1.1 mmol) in 4 ml of dioxane was rapidly added. After 5 min., the solvents were evaporated, and a solution of the residue in $CH_2Cl_2$ was extracted with salt $NaHCO_3$, NaCl and dried ($MgSO_4$). The product was purified by flash chromatography on a $2\times20$ cm $SiO_2$ column by first separating non-polar material with 30% ethyl acetate in petroleum ether (300 ml), and then eluting the carbamate with 5% methanol in chloroform. The product, 1 and 2 respectively, was obtained as an amorphous blue solid which was dissolved in 3 ml of $CH_2Cl_2$ and added dropwise to 30 ml of pet ether. In the case of each of 1 and 2, respectively, a solid product was obtained having the following properties:

MMC Benzyl Carbamate Disulfide 1:

yield 92% blue powder; mp 99° (dec); $^1H$—NMR (pyr—$d_5$) δ 1.95 (s,3H,$CH_3$), 3.15 (s,3H,$OCH_3$), 3.4–4.2 (m,6H), 4.6–5.0 (m,2H), 5.20 (s,2H,$ArCH_2$), 5.6 (dd,1H), 6.9–7.8 (m,7H,ArH), 8.35–8.5 (m,1H,ArH); IR (KBr) υ 340, 2920, 1890, 1600, 1552 $cm^{-1}$; uv/vis ($CH_3OH$) λ max 356 nm (log ε=4.31).

MMC Benzyl Carbamate Disulfide 2:

yield 63% blue powder; mp 96–98° $^1H$—NMR (pyr-$d_5$) δ 1.90 (s,3H,$CH_3$), 3.07 (s,3H,$OCH_3$), 3.4–3.55 (m,2H), 3.8–4.05 (m,3H), 4.6–5.0 (m,3H), 4.85 (s,3H), 5.35–5.70 (m,3H), 6.8–7.7 (m,7H,ArH), 8.35 (d,1H,ArH); IR (KBr) υ 3400, 1692, 1600, 1552 $cm^{-1}$; uv/vis ($CH_3OH$) ε max 365 nm (log λ=4.32).

Preparation of Hydroxysuccinimide Ester 6.

To a solution of 125 mg (0.205 mmol) of 1 in 5 ml of acetone was added 18 µl (0.205 mmol) of 3-mercaptopropionic acid. An additional 18 µl of 3-mercaptopropionic acid was added after 1h and the reaction was complete after a total of 1½ h. The solvent was removed under vacuum and the residue was purified by flash chromatography ($SiO_2$) using 10% methanol in methylene chloride as eluant. The acid (5) was used in the next step without further purification.

A solution of the acid (5, 0.186 mmol), N-hydroxysuccinimide (→mg, 0.372 mmol) and dicyclohexyl carbodiimide (77 mg, 0.372 mmol) in 2 ml of dry DMF was stirred for 3 hrs. The precipitate was filtered and washed with ethyl acetate. After removal of the solvents under vacuum, the residue was purified by preparative TLC ($SiO_2$) using 10% isopropanaol in methylene chloride as eluant. The hydroxysuccinimide ester (6) was obtained as a fine blue solid (26 mg). $^1H$—NMR (360 MHz, $CDCl_3$) δ 1.75 (s,3H,$CH_3$), 2.85 (s,4H, succinimide $CH_2$), 2.8–3.1 (m,4H), 3.81 (s,3H,$OCH_3$), 3.20 (m,1H), 3.27–3.55 (m,3.70 (q,1H), 4.0 (br s, 1H), 4.33 (t,1H), 4.40 (d,1H), 4.6–5.4 (m,6H), 7.4(q,4H,ArH).

Preparation of Hydroxysuccinimide Ester 8.

The hydroxysuccinimide ester 8 was prepared from the pyridyl disulfide 1 and 2-mercapto-2-methyl propionic acid as described for the synthesis of 6. A fine blue solid (55 mg) was obtained starting with 100 mg of 1. $^1H$—NMR (220 MHz,$CDCl_3$) δ 1.68 (s,6H, $2CH_3$), 1.77 (s,3H,$CH_3$), 2.83 (s,4H,succinimide $CH_2$), 3.20 (s,3H,$OCH_3$), 3.25–3.75 (m,6H), 4.2–5.3 (m,6H), 7.40 (q,4H,ArH).

Preparation of Hydroxysuccinimide Ester 10.

The hydroxysuccinimide ester 10 was prepared from the pyridyl disulfide 2 and 2-mercapto-2-methyl propionic acid as described for the synthesis of 6. The product, 10. was obtained as a blue solid (10 mg) starting with 71 mg of 2. $^1H$—NMR (220 MHz, $CDCl_3$) δ 1.53

(s,3H,CH$_3$), 1.61 (s,3H,CH$_3$), 1.78 (s,3H,CH$_3$), 2.90 (s,4H, succinimide CH$_2$), 3.20 (s,3H,OCH$_3$), 3.4–3.8 (m,6H), 4.21 (t,1H), 4.40 (d,1H), 4.50 (br s, 2H), 490 (q,1H), 5.2–5.4 (m,4H), 7.2–7.4 (m,2H,ArH), 7.80 (d,2H,ArH).

Preparation of Drug-antibody Conjugates 11–13.

Solutions of the hydroxysuccinimide esters, 6, 8, 10, (2.9–3.7mM) in acetonitrile were added to L6 antibody (2.61 mg/ml) in 1.5 ml of 50 mM borate buffer (pH 8.5) containing 100 mM NaCl at 30° C. The hydroxysuccinimide esters 8 and 10 (20-fold total molar excess) were added in four equal portions at 10 minute intervals while 6 (10-fold total molar excess) was added in two equal portions at 0 and 10 minutes. After 40 minutes, the precipitate was removed by centrifugation and the supernatants were dialyzed overnight against PBS at 4° C. The dialysates were gently rotated with about 0.5g SM-2 polystyrene beads (BioRad) for 10 min. at 4° C. and then sterile filtered to remove any drug that was not covalently attached to the antibody. HPLC analyses (described below) of the conjugates indicated that no free drug or free-drug derivatives were present. The composition of the conjugates thus obtained were determined by the drug absorbance at 365 nm ($\epsilon$=21086) and the antibody absorbance at 280 nm (Abs 280 nm, 1 mg/ml=1.4) and were as follows: 11, 0.86 mg/ml Ab (1.29mg total), drug/Ab=4.38/1; 12 0.70 mg/ml Ab (1.05 mg total), drug/Ab 5.14/1; 13, 1.07 mg/ml Ab (1.65 mg total), drug/Ab =5.25/1.

An anti-tumor drug-antibody conjugate wherein the drug component is the alcohol group containing drug etoposide, whereby the etoposide is bonded to the disulfide benzyl moiety by a carbonate linkage rather than a carbamate linkage, is prepared by following substantially the foregoing procedures by first providing an etoposide benzyl carbonate disulfide by substituting etoposide (162 mg, 0.275 mmol) for MMC and then using the resulting etoposide benzyl carbonate disulfide in the place of the MMC benzyl carbamate disulfide in the remaining steps of the conjugate preparation.

Of course, MMA, daunomycin, adriamycin and the other amino group containing drugs can be used in place of MMC in the foregoing examples.

Stability of Conjugates.

The conjugates 11–13 were diluted with an equal volume of growth media containing RPMI and 10% fetal calf serum. The solutions were incubated at 37° C. Portions (0.25 ml) were applied to protein-A columns (0.25 ml) at periodic intervals and the columns were washed with PBS to remove any unbound material. The bound conjugates were eluted with 100 mM acetic acid containing 150 mM NaCl (0.5 ml) and quickly neutralized. Spectrophotometric analysis was used to determine the composition of the conjugates.

REACTION OF CONJUGATES WITH DITHIOTHREITOL

To a solution of the drug-antibody conjugates, 11–13 in PBS, was added dithiothreitol (final conc. 0.2 mM). After 19 hrs at room temperature, aliquots were analyzed by HPLC, using a 10 cm Whatman Partasil 5 ODS-3 reverse phase (C-18) column and the following gradient system: 30% CH$_3$OH in 0.1% acetate (pH 6) to 95% CH$_3$OH in 6 min; continued for 8 min; flow rate 2 ml/min; monitored at 340 nm.

RESULTS AND DISCUSSION

Preparation of Conjugates.

Figure 2:
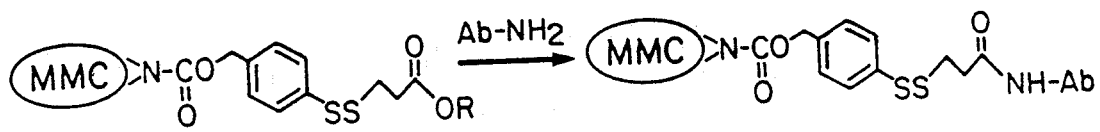
FIG. 2 illustrates the synthesis of a representative drug-monoclonal antibody conjugate according to this invention.
Figure 2:
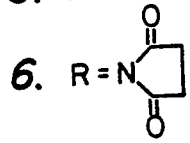
Figure 2:
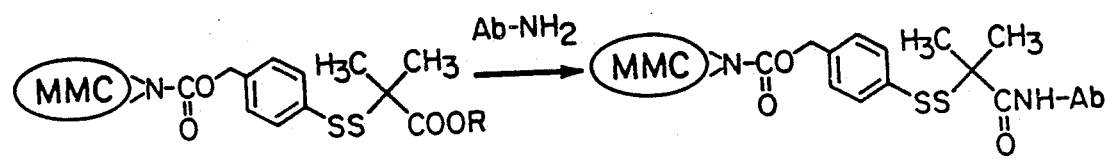
Figure 2:
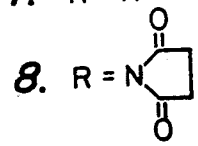
Figure 2:
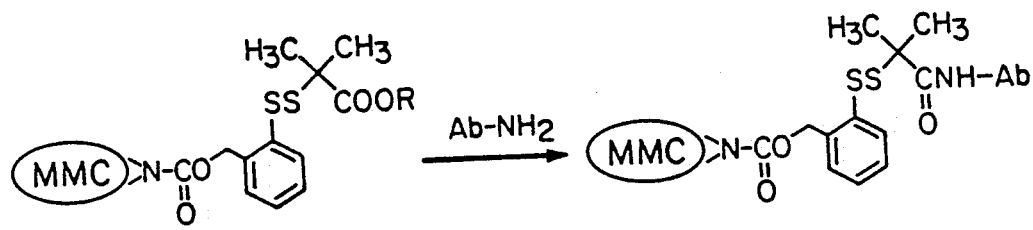
Figure 2:
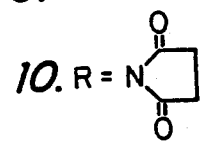

The hydroxysuccinimide esters 6, 8 and 10 were prepared from mitomycin C benzylcarbamate pyridyl disulfides 1 and 2 in a two-step process involving disulfide exchange with a thiol-substituted acid followed by esterification of the acid with N-hydroxysuccinimide (FIG. 2). Reaction of the hydroxysuccinimide esters with the antibody L6 at pH 8.5 resulted in the formation of antibody-MMC conjugates 11–13. The conjugates were free of any non-covalently attached MMC and were characterized by HPLC and uv/vis spectroscopy. It was possible to attach as many as six MMC molecules to L6 using the chemistry described. Presumably, amino groups on the antibody displace the hydroxysuccinimide esters on the activated drugs and amide bonds are formed between the antibody and the drug derivatives.

Release of Mitomycin C from the Conjugates.

The ability of benzyl carbamate disulfide drug derivatives to undergo drug elimination upon disulfide bond reduction has been studied in some detail (Senter supra). The presumed mechanism for the fragmentation reaction of disulfide bond in the conjugates, 11–13. would lead to the release of MMC.

Figure 3:
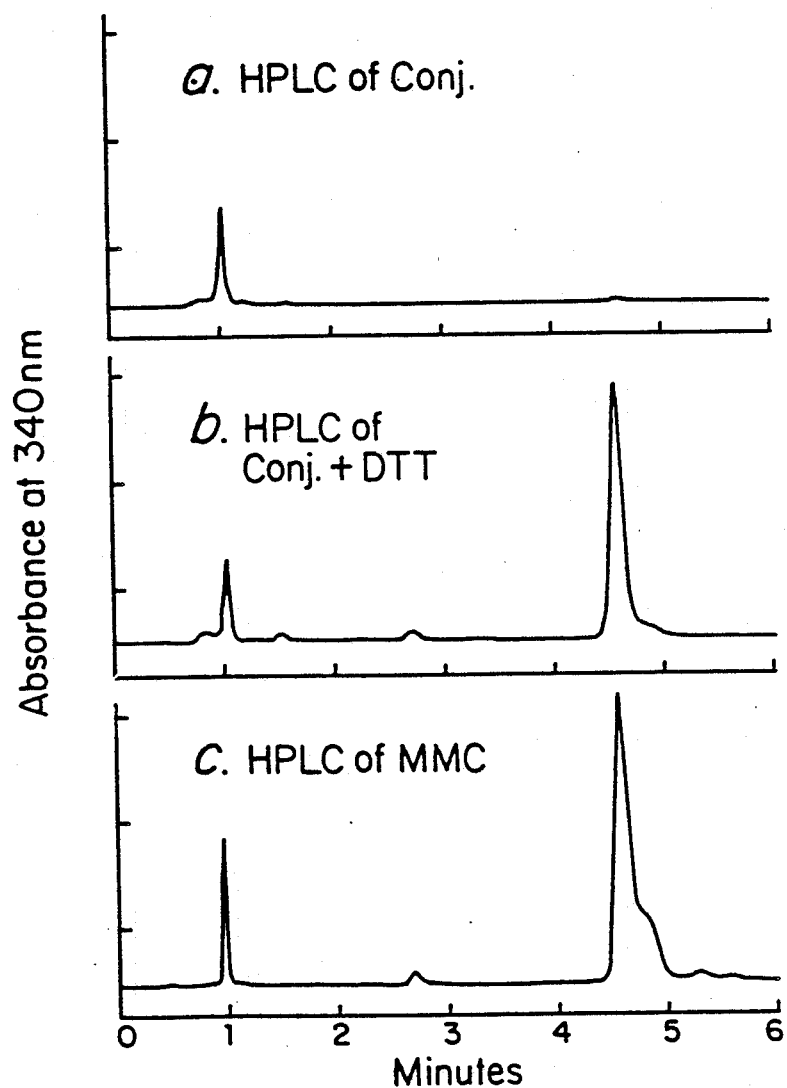
FIG. 3 illustrates HPLC comparative analytical results derivatives as prodrugs according to this invention.

The L6—MMC conjugate, 11, was reduced with excess dithiothreitol, and the reaction was monitored by HPLC. It was observed that MMC release occurred, as evidenced by comparison to an authentic sample (FIG. 3). In the absence of a reducing agent, the conjugates in PBS were completely stable under the reaction conditions.

It was of interest to determine whether steric hindrance of the disulfide bond would have an effect on the stability of the drug antibody conjugates. It has previously been reported that ricin-A chain immunotoxins with hindered disulfides were more stable in vitro than similar non-hindered immunotoxins (Worrell, et al., 1986).

The conjugates were incubated at 37° C. in 1:1 solutions of PBS and growth media containing RPMI and 10% fetal calf serum. The amount of drug that remained antibody bound was determined after the conjugates were re-isolated on a protein-A affinity column. After 24h, it was found that 11, 12 and 13 released 40%, 21% and 9% of the bound drug respectively. Therefore, increased conjugate stability can be achieved by increasing the degree to which the disulfide bond is hindered.

Binding and In Vitro Cytotoxicities of the Conjugates. The conjugates were tested for their ability to bind to receptors on the A549 lung carcinoma cell line. Fluorescence activated cell sorting indicated that all three conjugates bound to the cells just as well as the unmodified antibody. The chemistry used for drug attachment did not apparently affect the avidity of the antibody.

The cytotoxic activities of the conjugates on the A549 cell line was determined over a range of exposure times (Table 1). The least hindered conjugate, 11, displayed significant growth inhibition after only a 3h exposure, while the more hindered conjugates, 12 and 13. took considerably longer before a cytotoxic effect was observed. After 24 hours all three conjugates were highly cytotoxic. The IC-50 values obtained for conjugates 11, 12 and 13 after a 24 hour exposure were 55nM, 64nM, and 59nM respectively. The IC-50 value for free MMC after a 24 hour exposure was 50nM. Therefore, the conjugation chemistry preserves the activity of the drug.

REFERENCES

Endo, N., Kato, Y., Takeda, Y., Saito, M., Umemoto, N., Kishida, K., and Hara, T. In vitro cytotoxicity of a human serum-albumin-mediated conjugate of methotrexate with anti-MM46 monoclonal antibody. *Cancer Research* 47 1076–1080 (1987).

Gallego, J., Price, M. R., and Baldwin, R. W. Preparation of four daunomycin-monoclonal antibody 791T/36 conjugates with antitumor activity. *Int. J. Cancer.* 33, 737–744 (1984).

Hellstrom, I., Beaumier, P. L. and Helstrom, K. E. Antitumor effects of Lb, and IgG2A antibody that reacts with most human carcinomas *Proc. Natl. Acad. Sci.* 83, 7059–7063 (1986).

Moller, G. (Ed): Antibody carriers of drugs and toxins in tumor therapy. *Immunol. Rev.,* 62 (1982).

Ohkawa, K., Tsukada, Y., Hibi, N., Umemoto, N., and Hara, T. Selective in vitro and invivo growth inhibition against human yolk sac tumor cell lines by purified antibody against human α-fetoprotein conjugated with mitomycin C via human serum albumin. *Cancer Immunol. Immunother.* 23, 81–86 (1986).

Rowland, G. F., Simmonds, R. G., Gore, V. A., Marsden, C. H. and Smith, W. Drug localisation and growth inhibition studies of vindesine-monoclonal anti-CEA conjugates in a human tumor xenograft. *Cancer Immunol Immunother.* 21, 183–187 (1986).

Sartorelli, A. C. The role of mitomycin antibiotics in the chemotherapy of solid tumors. Biochem. Pharm. 35. 67–69 (1986).

Worrell, N. R., Cumber, A. J., Parnell, G. D., Mirza, A., Forrester, J. A. and Ross, W. C. J. Effect of linkage v variation on pharmacokinetics of ricin A chain-antibody conjugates in normal rats. *Anti-cancer Drug Design* 1, 179–188, (1986).

| Conjugate | % inhibition of colony formation | | | |
|---|---|---|---|---|
| 10 μg/ml antibody | 1h | 3h | 6h | 24h |
| 11 | 15% | 45% | 70% | 95% |
| 12 | 12% | 25% | 0% | 95% |
| 13 | 10% | 10% | 0% | 95% |

What is claimed is:

1. An anti-tumor drug-Monoclonal antibody conjugate having the general structural formula:

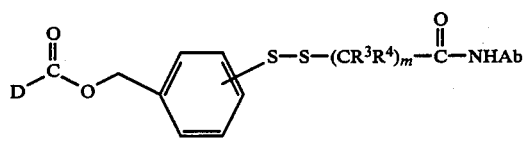

wherein:
D is an anti-tumor drug moiety having pendant to the backbone thereof a chemically reactive functional group, by means of which the drug backbone is bonded to the disulfide benzyloxycarbonyl group, derived from the group consisting of a primary amino group represented by the formula $R^1NH-$, a secondary amino group represented by the formula $R^1R^2N-$, and an alcohol group represented by the formula $R^1O-$;

$R^1$, when $R^1$ and $R^2$ are independent, is the backbone of said drug moiety when D is derived from the group consisting of a primary amino group, a secondary amino group, and an alcohol group;

$R^2$, when $R^1$ and $R^2$ are independent, is selected from unsubstituted and substituted and branched and straight-chain alkyl groups having 1–10 carbon atoms wherein the substitutent is selected from 1 to 3 alkoxy groups having 1 to 3 carbon atoms and 1 to 3 halo groups; unsubstituted and substituted phenyl wherein the substituent is selected from 1 to 3 alkyl groups having 1 to 3 carbon atoms, 1 to 3 alkoxy groups having 1 to 3 carbon atoms, and 1 to 3 halo groups; and unsubstituted and substituted phenalkyl wherein the phenyl moiety, when substituted, is substituted as defined above in the case of substituted phenyl and the alkyl moiety is a polyalkylene group having 1 to 3 carbon atoms;

$R^1$ and $R^2$, when taken together in a functional group derived from a secondary amine, represent the backbone of the drug moiety, D, having a divalent group chemically bonded to the nitrogen atom constituting said secondary amino group; and $R^3$ and $R^4$, independently, are selected from H and unsubstituted and substituted, and branched and straight-chain alkyl groups having 1–10 carbon atoms wherein the substitutent is selected from 1 to 3 alkoxy groups having 1 to 3 carbon atoms and 1 to 3 halo groups; unsubstituted and substituted phenyl wherein the substituent is selected from 1 to 3 alkyl groups having 1 to 3 carbon atoms, 1 to 3 alkoxy groups having 1 to 3 carbon atoms, and 1 to 3 halo groups; and unsubstituted and substituted phenylalkyl wherein the phenyl moiety, when substituted, is substituted as defined above in the case of substituted phenyl and the alkyl moiety is a polyalkylene group having 1 to 3 carbon atoms;

m is an integer selected from 1 to 10; and

Ab represents a monoclonal antibody having a pendent amino group; and the orientation of the group,

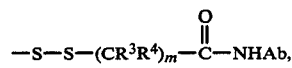

on the phenyl ring of the benzylcarbamate moiety is selected from the ortho- and para-positions.

2. An anti-tumor drug-monoclonal antibody conjugate according to claim 1 wherein the drug moiety, D, is a member selected from the group consisting of primary amine-containing and secondary amine-containing drugs.

3. An anti-tumor drug-monoclonal antibody conjugate according to claim 2 wherein the drug moiety, D, is a member selected from mitomycin-C, mitomycin-A, daunomycin, adriamycin, aminoptecin, actinomycin, bleomycin, and derivatives thereof.

4. An anti-tumor drug-monoclonal antibody conjugate according to claim 1 wherein, the drug moiety, D, is an alcohol group-containing drug.

5. An anti-tumor drug-monoclonal antibody conjugate according to claim 4 wherein the drug moiety, D, is etoposide.

6. A method for delivering to the site of tumor cells in a mammal having enhanced levels of endogenous reducing agents which reducing agents include at least one member of the group of NADH, NADPH and glutathione, an active anti-tumor drug having pendant to the backbone thereof a chemically reactive functional group selected from the group consisting of a primary amino group represented by the formula $R^1NH-$, a secondary amino group represented by the formula $R^1R^2N-$, and an alcohol group represented by the formula $R^1O$ wherein $R^1$ and $R^2$ are as defined in claim 1 above, comprising the steps of:

(a) administering to a mammal an antitumor effective amount of anti-tumor drug-monoclonal antibody conjugate according to claim 1;

(b) contacting the anti-tumor drug-monoclonal antibody conjugate from step (a) with endogenous reducing conditions, and (c) permitting the anti-tumor drug-monoclonal antibody conjugate to undergo reductive cleavage to release free drug from the conjugate.

* * * * *